United States Patent [19]

Reed

[11] Patent Number: 5,939,540
[45] Date of Patent: Aug. 17, 1999

[54] PLATELET SECRETORY TRANSPORT PROTEIN

[75] Inventor: Guy L. Reed, Winchester, Mass.

[73] Assignee: President and Fellows of Harvard College, Cambridge, Mass.

[21] Appl. No.: 08/946,412

[22] Filed: Oct. 7, 1997

Related U.S. Application Data

[60] Provisional application No. 60/027,678, Oct. 7, 1996.

[51] Int. Cl.[6] .......................... C07H 21/04; C12P 21/00; C12N 15/12; C12N 5/10
[52] U.S. Cl. ...................... 536/23.5; 435/69.1; 435/325; 435/320.1
[58] Field of Search ...................... 536/23.5; 435/320.1, 435/325, 69.1

[56] References Cited

FOREIGN PATENT DOCUMENTS

93/07174 4/1993 WIPO.
96/15149 5/1996 WIPO.

OTHER PUBLICATIONS

Vogel, F and Motulsky, V. in Human Genetics: Problems and Approaches. Vogel & Motulsky, eds. Springer–Verlag, Berlin. pp. 18–81, 1982.
Alberts, B et al. in Molecular Biology of the Cell: Second Edition. Adams, editor. Garland Publishing, New York. pp. 258–274, 1989.
Antin, JH et al. J. Immunol. 136(2):505–510, Jan. 15, 1986.
Bennett et al., "The Syntaxin Family of Vesicular Transport Receptors", Cell 74:863–873, 1993.
Brumell et al., "Subcellular Distribution of Docking/Fusion Proteins in Neutrophils, Secretory Cells with Multiple Exocytric Compartments", The Journal of Immunology 155:5750–5759, 1995.
Calakos et al., "Protein–Protein Interactions Contributing to the Specificity of Intracellular Vesicular Trafficking", Science 263:1146–1149, 1994.
Foley et al., "Continuous Culture of Human Lymphoblasts from Peripheral Blood of a Child with Acute Leukemia", Cancer 18:522–529, 1965.
Fujita et al., "Phosphorylation of Munc–18/n–Sec1rbSec1 by Protein Kinase C", The Journal of Biological Chemistry 271:7265–7268, 1996.
Garcia et al., "rbSec1A and B Colocalize with Syntaxin 1 and SNAP–25 throughout the Axon, but Are Not in a Stable Complex with Syntaxin", The Journal of Cell Biology 129:105–120, 1995.
Gengyo–Ando et al., "A Murine Neural–Specific Homolog Corrects Cholinergis Defects in Caenorhabditis elegans unc–18 Mutants", The Journal of Neuroscience 16:6695–6702, 1996.
Gengyo–Ando et al., "The C. elegans unc–18 Gene Encodes a Protein Expressed in Motor Neurons", Neuron 11:703–711, 1993.
Hata et al., "A Novel Ubiquitous Form of Munc–18 Interacts with Multiple Syntaxins", The Journal of Chemistry 270:13022–13028, 1995.

Holmsen et al., "Platelet Secretion and Energy Metabolism", pp. 524–545 in Hemostasis and Thrombosis, Third Edition, (Colman et al., ed.) 1994.
Katagiri et al., "A Novel Isoform of Syntaxin–binding Protein Homologous to Yeast Sec1 Expressed Ubiquitously in Mammalian Cells", The Journal of Biological Chemistry 270:4963–4966, 1995.
Novick et al., "Identification of 23 Complementation Groups Required for Post–translational Events in the Yeast Secretory Pathway", Cell 21:205–215, 1980.
Pevsner et al., "n–Sec1: A neural–specific syntaxin–binding protein", Proceedings of the National Academy of Sciences 91:1445–1449, 1994.
Pevsner et al., "Specificity and Regulation of a Synaptic Vesicle Docking Complex", Neuron 13:353–361, 1994.
Rothman, James E., "Mechanisms of intracellular protein transport", Nature 372:55–63, 1994.
Schulze et al., "rop, a Drosophila Homolog of Yeast Sec1 and Vertebrate n–Sec1/Munc–18 Proteins, Is a Negative Regulator of Neurotransmitter Release in Vivo", Neuron 13:1099–1108, 1994.
Tellam et al., "Characterization of Munc–18c and Syntaxin–4 in 3T3–L1 Adipocytes", The Journal of Biological Chemistry 272:6179–6186, 1997.
White, James G., "Anatomy and Structural Organization of the Platelet", pp.537–554 in Hemostasis and Thrombosis, Basic Principles and Clinical Practice, Second Edition. (Colman et al., ed).
Hata et al., "Synaptic Vesicle Fusion Complex Contains unc–18 Homologue Bound to Syntaxin", Nature 366:347–351, 1993.
Houng et al., "Identification and Molecular Cloning of PSTP: A Novel Platelet Secretory Transport Protein", Circulation vol. 94, No. 8, Suppl., Nov. 10, 1996, New York US, p. 1580.
Tellam et al., "Molecular Identification of Two Novel Munc–18 Isoforms Expressed in Non–neuronal Tissues", The Journal of Biological Chemistry 270:5857–5863, 1995.
EMBL Sequence Database, Heidelberg, DE Accession Nr.: R61138, May 29, 1995; L. Hillier et al., "Human cDNA sec1 homolog".
EMBL Sequence Database, Heidelberg, De Accession Nr.: D63506, Apr. 10, 1997, K. Gengyo–Ando, "Human mRNA for unc–18 Homologue".
Bush et al., "The Amyloid Precursor Protein of Alzheimer's Disease Is Released by Human Platelets", The Journal of Biological Chemistry 265:15977–15983, 1990.
Garcia et al., "A Rat Brain Sec1 Homologue Related to Rop and UNC18 Interacts with Syntaxin", Proc. Natl. Acad. Sci. USA 91:2003–2007, 1994.

*Primary Examiner*—David Saunders
*Assistant Examiner*—F. Pierre VanderVegt
*Attorney, Agent, or Firm*—Fish & Richardson P.C.

[57] ABSTRACT

Disclosed is a novel protein designated platelet secretory transport protein (PSTP). PSTP occurs in platelets and binds to syntaxin. An isolated DNA encoding PSTP, vectors and cells containing the DNA, and PSTP specific antibodies are also disclosed. A PSTP antibody can be used to target a compound to an activated platelet in a mammal for diagnostic or therapeutic purposes. Also disclosed is an in vitro screening method for identifying a compound that inhibits PSTP–syntaxin binding, and an in vitro method for identifying a compound that inhibits PSTP gene expression.

10 Claims, 5 Drawing Sheets

```
       -48         -38         -28         -18          -8
        *           *           *           *           *
AGCTCGCGCG  CCTGCAGGTC  GACACTAGTG  GATCCAAAGA  ATTCGGCACG 3          13          23          33          43
        *           *           *           *           *
AGGGAAGATG  GCGCCGCCGG  TGGCAGAGAG  GGGGCTAAAG  AGCGTCGTGT
      M   A  P  P    V  A  E  R    G  L  K     S  V  V>

53          63          73          83          93
        *           *           *           *           *
GGCAGAAGAT  AAAAGCAACA  GTGTTTGATG  ACTGCAAGAA  AGAAGGCGAA
  W  Q  K  I   K  A  T    V  F  D    D  C  K  K    E  G  E>

103         113         123         133         143
        *           *           *           *           *
TGGAAGATAA  TGCTTTTAGA  TGAATTTACC  ACTAAGCTTT  TGGCATCGTG
  W  K  I    M  L  L  D    E  F  T    T  K  L    L  A  S  C>

153         163         173         183         193
        *           *           *           *           *
TTGCAAAATG  ACAGATCTTC  TAGAAGAAGG  TATTACTGTT  GTAGAGAATA
  C  K  M    T  D  L  L    E  E  G    I  T  V    V  E  N>

203         213         223         233         243
        *           *           *           *           *
TTTATAAGAA  CCGTGAACCT  GTCAGACAAA  TGAAAGCTCT  TTATTTCATC
  I  Y  K  N    R  E  P    V  R  Q    M  K  A  L    Y  F  I>

253         263         273         283         293
        *           *           *           *           *
ACTCCGACAT  CAAAGTCTGT  AGATTGTTTC  TTACATGATT  TTGCAAGTAA
  T  P  T    S  K  S  V    D  C  F    L  H  D    F  A  S  K>

303         313         323         333         343
        *           *           *           *           *
ATCGGAGAAC  AAGTATAAAG  CAGCATATAT  TTACTTCACT  GACTTTTGCC
  S  E  N    K  Y  K    A  A  Y  I    Y  F  T    D  F  C>

353         363         373         383         393
        *           *           *           *           *
CTGATAATCT  CTTTAACAAA  ATTAAGGCTT  CTTGCTCCAA  GTCAATAAGA
  P  D  N  L    F  N  K    I  K  A    S  C  S  K    S  I  R>

403         413         423         433         443
        *           *           *           *           *
AGATGTAAAG  AAATAAATAT  TTCCTTCATT  CCACATGAAT  CTCAGGTGTA
  R  C  K    E  I  N  I    S  F  I    P  H  E    S  Q  V  Y>

453         463         473         483         493
        *           *           *           *           *
TACTCTTGAT  GTACCAGATG  CATTCTATTA  CTGTTATAGT  CCAGACCCTG
                                                (SEQ ID NO: 1)
```

503         513         523         533         543
             *           *           *           *           *
       GTAATGCAAA  GGGAAAAGAT  GCCATTATGG  AAACAATGGC  TGACCAGATA
        G   N   A   K   G   K   D   A   I   M   E   T   M   A   D   Q   I>

553         563         573         583         593
             *           *           *           *           *
       GTTACAGTGT  GTGCCACCTT  GGATGAAAAT  CCCGGAGTAA  GATATAAAAG
        V   T   V   C   A   T   L   D   E   N   P   G   V   R   Y   K   S>

603         613         623         633         643
             *           *           *           *           *
       TAAACCTCTA  GATAATGCCA  GTAAGCTTGC  ACAGCTTGTT  GAAAAAAAGC
        K   P   L   D   N   A   S   K   L   A   Q   L   V   E   K   K>

653         663         673         683         693
             *           *           *           *           *
       TTGAAGACTA  CTACAAGATT  GATGAAAAGA  GCCTAATAAA  GGGTAAAACT
        L   E   D   Y   Y   K   I   D   E   K   S   L   I   K   G   K   T>

703         713         723         733         743
             *           *           *           *           *
       CATTCACAGC  TCTTAATAAT  TGATCGTGGC  TTTGATCCTG  TGTCCACTGT
        H   S   Q   L   L   I   I   D   R   G   F   D   P   V   S   T   V>

753         763         773         783         793
             *           *           *           *           *
       CCTGCATGAA  CTGACCTTTC  AGGCAATGGC  ATATGATCTA  CTACCAATTG
        L   H   E   L   T   F   Q   A   M   A   Y   D   L   L   P   I>

803         813         823         833         843
             *           *           *           *           *
       AGAATGATAC  ATACAAATAT  AAAACAGATG  GAAAAGAAAA  GGAGGCCATC
        E   N   D   T   Y   K   Y   K   T   D   G   K   E   K   E   A   I>

853         863         873         883         893
             *           *           *           *           *
       CTTGAAGAAG  AAGATGACCT  CTGGGTTAGA  ATTCGACATC  GACATATTGC
        L   E   E   E   D   D   L   W   V   R   I   R   H   R   H   I   A>

903         913         923         933         943
             *           *           *           *           *
       GGTTGTGTTA  GAGGAAATTC  CCAAGCTTAT  GAAAGAAATT  TCATCAACAA
        V   V   L   E   E   I   P   K   L   M   K   E   I   S   S   T>

953         963         973         983         993
             *           *           *           *           *
       AGAAAGCAAC  AGAAGGAAAG  ACATCACTTA  GTGCTCTTAC  CCAGCTGATG
        K   K   A   T   E   G   K   T   S   L   S   A   L   T   Q   L   M>

```
AAAAAGATGC CCCATTTCCG AAAACAGATT ACTAAGCAAG TTGTCCATCT
 K  K  M   P  H  F  R   K  Q  I    T  K  Q    V  V  H  L>

1053       1063       1073       1083       1093
         *          *          *          *          *
TAACTTAGCA GAAGATTGCA TGAATAAGTT CAAGCTTAAT ATAGAAAAGC
 N  L  A   E  D  C    M  N  K  F   K  L  N    I  E  K>

1103       1113       1123       1133       1143
         *          *          *          *          *
TCTGCAAAAC TGAACAGGAC CTGGCACTTG GAACTGATGC AGAAGGACAG
 L  C  K  T  E  Q  D   L  A  L   G  T  D  A  E  G  Q>

1153       1163       1173       1183       1193
         *          *          *          *          *
AAGGTGAAAG ATTCCATGCG AGTACTCCTT CCAGTTCTAC TCAACAAAAA
 K  V  K   D  S  M  R   V  L  L   P  V  L    L  N  K  N>

1203       1213       1223       1233       1243
         *          *          *          *          *
TCATGATAAT TGTGATAAAA TAAGAGCAAT TCTACTTTAT ATCTTCAGTA
 H  D  N   C  D  K    I  R  A  I   L  L  Y    I  F  S>

1253       1263       1273       1283       1293
         *          *          *          *          *
TTAATGGAAC TACGGAAGAA AATTTGGACA GGTTGATCCA GAATGTAAAG
 I  N  G  T  T  E  E   N  L  D    R  L  I  Q   N  V  K>

1303       1313       1323       1333       1343
         *          *          *          *          *
ATAGAAAATG AGAGTGACAT GATTCGTAAC TGGAGTTACC TTGGTGTTCC
 I  E  N   E  S  D  M   I  R  N   W  S  Y    L  G  V  P>

1353       1363       1373       1383       1393
         *          *          *          *          *
CATTGTTCCC CAATCTCAAC AAGGCAAACC GTTAAGAAAG GATCGGTCTG
 I  V  P   Q  S  Q  Q   G  K  P   L  R  K    D  R  S>

1403       1413       1423       1433       1443
         *          *          *          *          *
CAGAAGAAAC TTTTCAGCTC TCTCGGTGGA CACCTTTTAT CAAAGATATT
 A  E  E  T   F  Q  L   S  R  W   T  P  F  I   K  D  I>

1453       1463       1473       1483       1493
         *          *          *          *          *
ATGGAGGATG CTATTGATAA TAGATTAGAT TCAAAAGAAT GGCCATATTG
 M  E  D   A  I  D  N   R  L  D    S  K  E   W  P  Y  C>

1503       1513       1523       1533       1543
         *          *          *          *          *
TTCCCAGTGT CCAGCAGTAT GGAATGGTTC AGGAGCTGTA AGTGCTCGCC
 S  Q  C   P  A  V    W  N  G  S   G  A  V    S  A  R>

```
                *              *              *              *              *
        AGAAACCCAG    AGCTAATTAT    TTAGAAGACC    GAAAAAATGG    GTCAAAGCTG
        Q  K  P  R    A  N  Y      L  E  D       R  K  N  G    S  K  L>

1603           1613           1623           1633           1643
              *              *              *              *              *
        ATTGTTTTTG    TAATTGGAGG    GATCACATAC    TCTGAAGTGC    GTTGTGCTTA
        I  V  F       V  I  G  G    I  T  Y      S  E  V       R  C  A  Y>

1653           1663           1673           1683           1693
              *              *              *              *              *
        TGAAGTTTCT    CAGGCACATA    AATCCTGTGA    AGTTATTATT    GGTTCTACAC
        E  V  S       Q  A  H  K    S  C  E      V  I  I       G  S  T>

1703           1713           1723           1733           1743
              *              *              *              *              *
        ATGTTTTAAC    ACCCAAAAAG    CTGTTGGATG    ATATAAAGAT    GCTGAATAAA
        H  V  L  T    P  K  K       L  L  D       D  I  K  M    L  N  K>

1753           1763           1773           1783           1793
              *              *              *              *              *
        CCCAAGGATA    AAGTCTCCTT    AATTAAAGAT    GAATAGCATT    TCTTTTTGGA
        P  K  D       K  V  S  L    I  K  D       E  *

1803           1813           1823           1833           1843
              *              *              *              *              *
        GGGTTTAGAG    ATTCTTACTA    ATATGTTGAA    CTAAAATAGA    AAGAAAATGT 1853           1863           1873           1883           1893
              *              *              *              *              *
        TGCTGTCATG    TAATTTAAAC    AATGTAAATA    TTTTATGGAA    TAATGGCTTT
        >

1903           1913           1923           1933           1943
              *              *              *              *              *
        TCAAATACAT    TTCTTAAGGA    ACTGTTTATG    ATTATTACTG    GATTTGTCAT 1953           1963           1973           1983           1993
              *              *              *              *              *
        TTTTGATAAT    TTAAATATTG    CTGCTGCTTT    GTAGATGATG    AGAAGAAATG 2003           2013           2023           2033           2043
              *              *              *              *              *
        TTAAAGTGCT    TTCTAAAAGG    AAATTTTTTC    ACCTTTGGAG    GAGAATATAT 2053           2063           2073           2083           2093
              *              *              *              *              *
        TAGAGTTGTG    GGTAATTTTT    CACAGCCACC    TATGTACATA    CTAATTACCC
```

FIG. 1D

```
            2103       2113       2123       2133       2143
             *          *          *          *          *
        ATTGGATACT TATATCTAAA AGTCTCATGC TGAAGTATAG TTTTTGGGAA 2153       2163       2173       2183       2193
             *          *          *          *          *
        AGAATGATTT TAAATAAAGA GATTGTAAAA GTAAAAAACT GTAAATGTAT 2203       2213       2223       2233       2243
             *          *          *          *          *
        ATGTATGATA GAATTGTTTC CTCTAAGTGT AGTTTTTCTT TCAACTAAAA 2253       2263       2273       2283       2293
             *          *          *          *          *
        TTCAGTTTAT GTGTAAAATA ATTCAGTCAT TAATAGAAAT GGAGTGATTT 2303       2313       2323       2333       2343
             *          *          *          *          *
        CACAGTGTGT ACTGTTTTGC CACATACTTC TAAAGAACAC AATTTTATAT 2353       2363       2373       2383       2393
             *          *          *          *          *
        AATTTTGAAA TCATGTATGT TTAAATTAGA AAACCAAAAA TCATGAACAT 2403       2413       2423       2433       2443
             *          *          *          *          *
        TCTAAGAGAA AATAAATATA GAATTTAAAA AATTAAAAAA AAAAAAAAAA

AAAA
```

FIG. 1E

PLATELET SECRETORY TRANSPORT PROTEIN

CROSS REFERENCE TO RELATED APPLICATION

This application claims benefit from provisional application Ser. No. 60/027,678, filed Oct. 7, 1996.

BACKGROUND OF THE INVENTION

The invention relates to proteins involved in platelet secretion.

Vascular injury can cause a rapid loss of the protein, fluid, and cellular components of the blood. Therefore, animals have developed rapid responses to stop bleeding and to initiate repair of blood vessels. These rapid responses are initiated by the platelet, a highly specialized cell that reacts to vascular injury. Normally, platelets circulate in the blood as quiescent and nonadherent cells, monitoring the integrity of blood vessels. In response to vascular injury, platelets adhere to each other and to de-endothelialized areas, and they undergo activation.

Platelet activation results in morphologic and functional changes in the cell. When platelets are activated by thrombin or other agonists, there is a marked increase in the level of intracellular calcium ions, and an increase in phosphorylation of intracellular proteins. Upon activation, platelet granules fuse with the cell membrane. This leads to platelet secretion of effector molecules, including platelet-derived growth factor, TGF-$\beta$, clotting factor V, fibrinogen, arachidonate, ADP, and P-selectin. Such molecules secreted by activated platelets play critical roles in the complex cellular and biochemical processes that reduce blood loss and begin the process of vascular repair.

The cellular and biochemical processes initiated by platelets in response to vascular injury can be lifesaving, but in the absence of such injury these same processes can be deleterious. For example, unregulated arterial platelet thrombosis can occlude the blood supply to organs and lead to strokes, heart attacks, and limb necrosis.

SUMMARY OF THE INVENTION

A novel protein, designated platelet secretory transport protein (PSTP), is identified and characterized. PSTP is expressed in activated platelets, binds to syntaxin, and is involved in activation-dependent platelet secretion.

The invention includes an isolated DNA containing a nucleotide sequence that: (1) encodes a PSTP that shares at least 80% sequence identity with SEQ ID NO:2, (2) occurs naturally in platelets, and (3) binds to syntaxin. The naturally occurring PSTP may be expressed at an increased level by activated platelets compared to its expression level in resting platelets. Preferably, the isolated DNA includes a nucleotide sequence that defines a DNA whose complement hybridizes under stringent hybridization conditions to a DNA having a nucleotide sequence consisting of SEQ ID NO:1. More preferably, the DNA includes the coding sequence of SEQ ID NO:1 (human PSTP), or a degenerate variant of SEQ ID NO:1.

The invention also includes a vector containing the above-described isolated DNA, and a cell containing such a vector. The cell can be prokaryotic (e.g., E. coli) or eukaryotic (e.g., a yeast cell or a mammalian cell). Preferably, the cell expresses the polypeptide encoded by SEQ ID NO:1.

The invention also includes a substantially pure, naturally-occurring PSTP that: (1) shares at least 80% sequence identity with SEQ ID NO:2, (2) occurs naturally in platelets, and (3) binds to syntaxin. Preferably, the sequence identity shared with SEQ ID NO:2 is at least 85%. More preferably, the sequence identity is at least 90%, and most preferably it is at least 95%. Preferably, the amino acid sequence of the PSTP differs from SEQ ID NO:2 solely by conservative amino acid substitutions, i.e., substitution of one amino acid for another of the same class, or by non-conservative substitutions, deletions, or insertions located at positions that do not destroy the function of the protein. Preferably, it is a mammalian protein. More preferably, the amino acid sequence of the PSTP consists of SEQ ID NO:2 (human PSTP). The invention includes PSTP with or without a signal sequence.

The invention also includes an antibody that binds specifically to a protein the amino acid sequence of which is SEQ ID NO:2. The antibody can be polyclonal or monoclonal. The antibody can be conjugated to a detectable label.

The invention also includes a method for targeting a compound to an activated platelet in a mammal, comprising administering to the mammal the compound conjugated to a PSTP-specific antibody.

The invention also includes a method for locating a platelet thrombus in a mammal. The method includes the steps of: (a) administering to the mammal an antibody that binds specifically to the protein defined by SEQ ID NO:2, and (b) detecting where the antibody binds in the mammal.

The invention also includes an in vitro screening method for identifying a compound that modulates PSTP interaction with syntaxin. The method includes the steps of: (a) providing a PSTP sample solution; (b) adding to the sample solution a candidate compound; (c) adding to the sample solution a syntaxin sample; and (d) detecting an increase or decrease in PSTP-syntaxin binding in the presence of the candidate compound, compared to PSTP-syntaxin binding in the absence of the candidate compound.

The invention also includes an in vitro screening method for identifying a compound that modulates the binding of SNAP-25 to syntaxin in the presence of PSTP. The method includes the steps of: (a) providing a PSTP sample solution; (b) adding to the sample solution a SNAP-25 sample; (c) adding to the sample solution a candidate compound; (d) adding to the sample solution a syntaxin sample; and (e) detecting an increase or decrease in SNAP-25-syntaxin binding in the presence of the candidate compound, compared to SNAP-25-syntaxin binding in the absence of the candidate compound.

The invention also includes an in vitro screening method for identifying a compound that modulates PSTP gene expression. The screening method includes the steps of: (a) providing a test cell; (b) contacting the test cell with a candidate compound; and (c) detecting an increase or decrease in the level of PSTP gene expression in the presence of the candidate compound, compared to the level of PSTP gene expression in the absence of the candidate compound.

The invention also includes method of making a platelet secretory transport protein. The method includes the steps of: (a) providing a cell transformed with an isolated DNA comprising a nucleotide sequence that encodes a protein, the amino acid sequence of which is SEQ ID NO:2 ; (b) culturing the cell; and (c) collecting the protein encoded by the nucleotide sequence.

The invention also includes a method for purifying syntaxin. The method includes the steps of conjugating a PSTP protein to a solid support, contacting a syntaxin-containing solution with the solid support, and then eluting syntaxin from the solid support. Preferably, the solid support consists of beads or particles used in column chromatography. Preferably, the method includes a washing step prior to the eluting step.

As used herein, "high stringency" means the following: hybridization at 42° C. in the presence of 50% formamide; a first wash at 65° C. with about 2×SSC containing 1% SDS; followed by a second wash at 65° C. with 0.1×SSC.

As used herein, "isolated DNA" means DNA free of the genes that flank the gene of interest in the genome of the organism in which the gene of interest naturally occurs. The term therefore includes a recombinant DNA incorporated into a vector, into an autonomously replicating plasmid or virus, or into the genomic DNA of a prokaryote or eukaryote. It also includes a separate molecule such as a cDNA, a genomic fragment, a fragment produced by polymerase chain reaction (PCR), or a restriction fragment. It also includes a recombinant nucleotide sequence that is part of a hybrid gene, i.e., a gene encoding a fusion protein. Also included is a recombinant DNA that includes a portion of SEQ ID NO:1 and that encodes an alternative splice variant of PSTP.

As used herein, "operably linked" means incorporated into a genetic construct so that expression control sequences effectively control expression of a gene of interest.

As used herein, "protein" means any peptide-linked chain of amino acids, regardless of length or post-translational modification, e.g., glycosylation or phosphorylation.

As used herein, "PSTP" means: (1) a protein, the amino acid sequence of which is SEQ ID NO:2, or (2) a protein that shares at least 80% amino acid sequence identity with SEQ ID NO:2, occurs naturally in platelets, and binds to syntaxin.

As used herein, "sequence identity" means the percentage of identical subunits at corresponding positions in two sequences when the two sequences are aligned to maximize subunit matching, i.e., taking into account gaps and insertions. When a subunit position in both of the two sequences is occupied by the same monomeric subunit, e.g., if a given position is occupied by an adenine in each of two DNA molecules, then the molecules are identical at that position. For example, if 7 positions in a sequence 10 nucleotides in length are identical to the corresponding positions in a second 10-nucleotide sequence, then the two sequences have 70% sequence identity. Preferably, the length of the compared sequences is at least 60 nucleotides, more preferably at least 75 nucleotides, and most preferably 100 nucleotides. Sequence identity is typically measured using sequence analysis software (e.g., Sequence Analysis Software Package of the Genetics Computer Group, University of Wisconsin Biotechnology Center, 1710 University Avenue, Madison, Wis. 53705).

As used herein, "PSTP-specific antibody" means an antibody that binds to a protein, the amino acid sequence of which is SEQ ID NO:2 and does not bind to other naturally proteins. The term includes polyclonal and monoclonal antibodies.

As used herein, "substantially pure protein" means a protein separated from components that naturally accompany it. Typically, the protein is substantially pure when it is at least 60%, by weight, free from the proteins and other naturally-occurring organic molecules with which it is naturally associated. Preferably, the purity of the preparation is at least 75%, more preferably at least 90%, and most preferably at least 99%, by weight. A substantially pure PSTP protein can be obtained, for example, by extraction from a natural source, by expression of a recombinant nucleic acid encoding an PSTP polypeptide, or by chemical synthesis. Purity can be measured by any appropriate method, e.g., column chromatography, polyacrylamide gel electrophoresis, or HPLC analysis. A chemically synthesized protein or a recombinant protein produced in a cell type other than the cell type in which it naturally occurs is, by definition, substantially free from components that naturally accompany it. Accordingly, substantially pure proteins include those having sequences derived from eukaryotic organisms but synthesized in E. coli or other prokaryotes.

As used herein, "test cell" means a cell that expresses a PSTP gene, in the absence of a PSTP gene repressor. Preferably, the PSTP gene in the test cell is under the control of a promoter that is naturally associated with a PSTP gene.

As used herein, "vector" means a replicable nucleic acid construct, e.g., a plasmid or viral nucleic acid.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, the preferred methods and materials are described below. All publications, patent applications, patents, and other references mentioned herein are incorporated by reference in their entirety. In case of conflict, the present document, including definitions, will control. Unless otherwise indicated, materials, methods, and examples described herein are illustrative only and not intended to be limiting.

Various features and advantages of the invention will be apparent from the following detailed description and from the claims.

BRIEF DESCRIPTION OF THE DRAWING

FIGS. 1A–1E is the nucleotide sequence of a human PSTP cDNA and the deduced amino acid sequence.

DETAILED DESCRIPTION

A human PSTP cDNA has been cloned and sequenced. The PSTP cDNA contains a 1.8 kilobase open reading frame that encodes a protein containing 592 amino acid residues. The deduced amino acid sequence of PSTP includes a putative signal peptide, eight potential N-linked glycosylation sites, and threonine and tyrosine phosphorylation sites. Northern analyses, carried out with a 0.5 kilobase PSTP probe, identified a 2.7 kilobase mRNA transcript in a megakaryoblastic (DAMI) cell line. A polyclonal antibody raised against a recombinant fragment of PSTP binds to a 70 kDa band on immunoblots of human platelet lysates and DAMI cell lysates.

Inhibiting Platelet Secretion

Sequence analysis shows PSTP to be related to proteins encoded by the Sec-1 gene family. Those proteins interact with syntaxins and other proteins, e.g., SNAP-25 , in regulated exocytosis (Rothman, Nature 372:55–63). Such regulated exocytosis is exemplified by regulated neuro-vesicle release from neurons, at synapses.

Platelet secretion is a type of regulated exocytosis, and PSTP binds to syntaxin. Therefore, without intending to be bound by theory in the present invention, it is expected that binding of a platelet syntaxin to PSTP affects platelet secretion. Therefore, it is expected that a compound that modulates syntaxin binding to PSTP, or syntaxin binding to SNAP-25 in the presence of PSTP, will modulate platelet secretion and its effects, e.g., platelet thrombus formation. Alternatively, a compound that modulates PSTP gene expression can be used to modulate platelet secretion and its effects.

Expression Control Sequences and Vectors

In some embodiments of the invention, PSTP DNA is cloned into an expression vector, i.e., a vector wherein PSTP DNA is operably linked to expression control sequences. The need for, and identity of, expression control sequences will vary according to the type of cell in which the PSTP DNA is to be expressed. Generally, expression control sequences include a transcriptional promoter, enhancer, suitable mRNA ribosomal binding sites, and sequences that terminate transcription and translation. Suitable expression control sequences can be selected by one of ordinary skill in the art. Standard methods can be used by the skilled person to construct expression vectors. See generally, Sambrook et al., 1989, *Molecular Cloning: A Laboratory Manual* (2nd Edition), Cold Spring Harbor Press, Cold Spring Harbor, N.Y. Vectors useful in this invention include plasmid vectors and viral vectors. Preferred viral vectors are those derived from retroviruses, adenovirus, adeno-associated virus, SV40 virus, or herpes viruses.

PSTP DNA In Vitro

In some embodiments of the invention, PSTP DNA is introduced into, and expressed in, a prokaryotic cell. A preferred prokaryotic cell is *Escherichia coli*. For expression in a prokaryotic cell, PSTP DNA can be integrated into a bacterial chromosome or expressed from an extrachromosomal DNA.

In other embodiments of the invention, the PSTP DNA is introduced into, and expressed in, a eukaryotic cell in vitro. Eukaryotic cells useful for expressing PSTP DNA in vitro include, but are not limited to, COS, CHO, and Sf9 cells. Transfection of the eukaryotic cell can be transient or stable. The PSTP DNA can be, but is not necessarily, integrated into a chromosome of the eukaryotic cell.

Signal Peptide

The scope of the invention encompasses PSTP with or without a signal peptide, and an isolated DNA molecule encoding PSTP with or without a signal peptide. Using the PSTP nucleotide sequence, and guidance provided by the present disclosure, one of ordinary skill in the art can determine the first amino acid of mature human PSTP, i.e., PSTP without its signal peptide.

Mature PSTP is preferably produced by expression of a recombinant DNA. A recombinant DNA encoding mature PSTP can be produced, for example, by: (1) cleaving a PSTP cDNA at a restriction site located within, and near the 5' end of, the nucleotide sequence encoding the mature PSTP, thereby producing a truncated PSTP cDNA; and (2) restoring a complete coding sequence for the mature PSTP by ligating a synthetic DNA fragment to the truncated cDNA. A DNA construct used to produce recombinant mature PSTP must include a translation initiation codon (i.e., ATG) immediately preceding the first codon of the mature PSTP coding sequence. Optionally, the amino-terminal methionine residue can be removed by a cell used for production of recombinant mature PSTP, or by chemical cleavage. Mature PSTP can also be obtained by conventional peptide synthesis, e.g., solid phase synthesis.

PSTP-Specific Antibody

Some embodiments of this invention include a PSTP-specific antibody. Standard protocols for monoclonal and polyclonal antibody production are known and can be carried out by one of ordinary skill in the art, to obtain antibodies useful in this invention.

The invention encompasses not only an intact monoclonal antibody, but also an immunologically active antibody fragment. Examples of such a fragment include a Fab or (Fab)$_2$ fragment, an engineered single chain Fv molecule, and a chimeric antibody. Typically, a chimeric antibody includes a variable region of a non-human antibody, e.g., a murine variable region, and a constant region of a human antibody.

Antibody Label

In some embodiments of the invention, the PSTP-specific antibody includes a detectable label. Various types of detectable labels can be linked to, or incorporated into, an antibody of this invention. Examples of useful label types include radioactive, non-radioactive isotopic, fluorescent, chemiluminescent, paramagnetic, enzyme, or colorimetric.

Examples of useful enzyme labels include malate hydrogenase, staphylococcal nuclease, delta-5-steroid isomerase, alcohol dehydrogenase, alpha-glycerol phosphate dehydrogenase, triose phosphate isomerase, peroxidase, alkaline phosphatase, asparaginase, glucose oxidase, beta-galactosidase, ribonuclease, urease, catalase, glucose-6-phosphate dehydrogenase, and glucoamylase, acetylcholinesterase. Examples of useful radioisotopic labels include $^3$H, $^{125}$I, $^{131}$I, $^{32}$P, $^{35}$S, and $^{14}$C. Examples of useful fluorescent labels include fluorescein, rhodamine, phycoerythrin, phycocyanin, allophycocyanin, and fluorescamine. Examples of useful chemiluminescent label types include luminal, isoluminal, aromatic acridinium ester, imidazole, acridinium salt, oxalate ester, luciferin, luciferase, and aequorin.

Suitable labels can be coupled to, or incorporated into antibodies or antibody fragments through standard techniques known to those of ordinary skill in the art. Typical techniques are described by Kennedy et al., (1976) *Clin. Chim. Acta* 70, 1–31; and Schurs et al., (1977) *Clin. Chim. Acta* 81, 1–40. Useful chemical coupling methods include those that use on glutaraldehyde, periodate, dimaleimide, m-maleimido-benzyl-N-hydroxy-succinimide ester.

In Vitro Diagnostic Methods

The invention encompasses a method of detecting an activated platelet in a biological sample, which includes the steps of contacting the sample with a labelled PSTP-specific antibody, and determining whether the antibody binds to a component of the sample. Antibody binding indicates that the sample contains a PSTP polypeptide, and consequently, an activated platelet.

The invention includes a method of detecting a leukemic cell or a megakaryoblastic cell in a biological sample, which includes the steps of contacting the sample with a labelled PSTP-specific antibody, and determining whether the antibody binds to a component of the sample. Antibody binding indicates that the sample contains a leukemic cell or a megakaryoblastic cell.

PSTP antibody binding is detected by means of the detectable label on the antibody. The detection technique will depend on the type of label used. Selection of a suitable detection technique for a particular type of label is within ordinary skill in the art.

In Vivo Diagnostic and Therapeutic Methods

An antibody of this invention can be used as a diagnostic tool to localize a platelet thrombus in a mammal, e.g., a human patient suspected of having undesirable blood clots. The method includes administering to the mammal the labelled antibody, and determining where in the animal the label localizes. Detection of the label at a given site in the animal indicates the existence of a platelet thrombus at that site.

A preferred label for a PSTP-specific antibody used for in vivo diagnosis is a paramagnetic isotope. Various paramagnetic isotopes are useful for magnetic resonance imaging. For discussions on in vivo nuclear magnetic resonance imaging, see, for example, Schaefer et al., (1989) *JACC* 14, 472–480; Shreve et al., (1986) *Magn. Reson. Med.* 3, 336–340; Wolf, G. L., (1984) *Physiol. Chem. Phys. Med. NMR* 16, 93–95; Wesbey et al., (1984) *Physiol. Chem. Phys. Med. NMR* 16, 145–155; Runge et al., (1984) *Invest. Radiol.* 19, 408–415.

An antibody of the invention can also be used in a form of therapy to target a compound to an activated platelet in a mammal. The method includes the steps of administering to an animal a composition containing the compound linked to a PSTP-specific antibody.

Preferably, the targeted compound is a thrombolytic agent (to dissolve a thrombus), an anti-thrombotic agent (to prevent thrombus formation), an antiproliferative agent (to inhibit cell proliferation), or an anti-migration agent (to inhibit migration of cells which contribute to the obstruction of a blood vessel at a thrombus site). Thrombolytic agents include urokinase, prourokinase, streptokinase, tissue-type plasminogen activator, staphylokinase, and vampire bat tissue plasminogen activator. Anti-thrombotic agents include heparin, hirudin, and inhibitors of Factor Xa or Factor 5a. Anti-proliferative agents include inhibitors of platelet-derived growth factor or heparin binding growth factor. Anti-migration agents include specific inhibitors of urokinase or integrin function.

The therapeutic agents can be linked to a PSTP-specific antibody using a disulfide bond or a covalent crosslinking agent. The antibody and polypeptide therapeutic agent can also be produced recombinantly, as a fusion protein.

PSTP Isolation

Platelets were isolated from whole blood by differential centrifugation (Mustard et al., 1989, *Meth. Enzymol.* 169:3–11). Platelets to be activated were resuspended in 50 ml of a modified Tyrode's buffer (3.5 mM HEPES, 137 mM NaCl, 2.7 mM KCl, 5.5 mM glucose, 3 mM $NaH_2PO_4$, 2 mM $CaCl_2$ and 1 mM $MgCl_2$, without bovine serum albumin) at a concentration of $7.4 \times 10^{10}$ cells/ml. Platelets to be kept resting were resuspended at the same concentration in the modified Tyrode's buffer containing 1 mM EDTA without $CaCl_2$ and $MgCl_2$. NHS-LC-biotin (sulfosuccinimidyl 6-(biotinamido) hexanoate, Pierce, Rockford, Ill.) was dissolved at a concentration 40 mg in 1 ml of $H_2O$ containing 1% DMSO. Platelets were activated by the addition of 0.15 units of thrombin and incubated at 37° C. for 5 min. The activated platelets were isolated by differential centrifugation, washed once in the same buffer and resuspended in 50 ml. The NHS-LC biotin solution (500 µl) was added to the resting and activated platelets, and the solutions were allowed to mix on a rotator for 2 hours, at room temperature. The tubes were centrifuged at 3000 rpm, for 20 minutes. The supernatant was removed and the platelet pellet was resuspended in 50 ml of their respective buffers, and then recentrifuged. The wash was repeated again, and the platelets were resuspended in 50 ml of Tyrode's buffer without BSA, containing 7% DMSO. Aliquots (1 ml) were frozen at −70° C., for later use.

Thrombin-activated, biotinylated platelets were lysed by the addition of 1% (final) Triton X-100 (Sigma, St. Louis, Mo.) containing 100 units/ml aprotinin, and 10 µM leupeptin. After centrifugation at 13,200 rpm for 5 minutes, in microfuge tubes, the supernatant was added to a streptavidin column (1 ml, Pierce, Rockford, Ill.). The column was washed with phosphate buffered saline (PBS) until the absorbance at 280 nm was below 0.01. The bound biotinylated proteins were eluted with 8 M guanidine pH 1.5. The pH of the fractions was neutralized, and the fractions were dialyzed against PBS containing 1% Triton X-100.

A male New Zealand rabbit was repeatedly immunized four times at 6 week intervals, with approximately 1 mg of biotinylated platelet proteins. Antiplatelet antiserum was obtained from the immunized rabbit by standard methods. The antiplatelet antiserum was absorbed against an *E. Coli* Y1090 lysate as described by Sambrook, et al. (supra).

The antiplatelet antibody was used to screen a custom CCRF (human leukemic cell line; Foley et al., 1965, *Cancer* 18:522–529) cDNA library (Stratagene, La Jolla, Calif.) as described by Sambrook et al. (supra). In the primary screen of ~300,000 phage particles, PSTP was identified as an immunoreactive plaque. The plaque was purified to homogeneity by repetitive screening, and shown not to be reactive with non-immune rabbit antibody. The PSTP phagemid DNA was isolated by standard methods and subjected to double stranded DNA sequencing (Sanger et al., 1977, *Proc. Natl. Acad. Sci. USA* 74:5463–5467).

Desposit Statement

The subject cultures have been deposited under conditions that assure that access to the cultures will be available during the pendency of the patent application disclosing them to one determined by the Commissioner of Patents and Trademarks to be entitled thereto under 37 CFR 1.14 and 35 USC 122. The date of deposit was Oct. 4, 1996. The ATCC accession number is 97745. The deposits are available as required by foreign patent laws in countries wherein counterparts of the subject application, or its progeny, are filed. However, it should be understood that the availability of a deposit does not constitute a license to practice the subject invention in derogation of patent rights granted by governmental action.

Further, the subject culture deposits will be stored and made available to the public in accord with the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them.

It should be noted that the deposits designate the encoded protein as "APP-3" instead of "PSTP." The terms "APP-3" and "PSTP" are synonymous, for purposes of the present invention and the microorganism deposits made in connection therewith.

Other embodiments are within the following claims.

SEQUENCE LISTING (1) GENERAL INFORMATION:

(iii) NUMBER OF SEQUENCES: 2

(2) INFORMATION FOR SEQ ID NO:1:

(i) SEQUENCE CHARACTERISTICS:
    (A) LENGTH: 2504 base pairs
    (B) TYPE: nucleic acid
    (C) STRANDEDNESS: single
    (D) TOPOLOGY: linear (ii) MOLECULE TYPE: Other (ix) FEATURE:
    (A) NAME/KEY: Coding Sequence
    (B) LOCATION: 58...1833
    (D) OTHER INFORMATION:

(xi) SEQUENCE DESCRIPTION: SEQ ID NO:1:

```
AGCTCGCGCG CCTGCAGGTC GACACTAGTG GATCCAAAGA ATTCGGCACG AGGGAAG ATG      60
                                                                 Met
                                                                  1

GCG CCG CCG GTG GCA GAG AGG GGG CTA AAG AGC GTC GTG TGG CAG AAG       108
Ala Pro Pro Val Ala Glu Arg Gly Leu Lys Ser Val Val Trp Gln Lys
          5                  10                  15

ATA AAA GCA ACA GTG TTT GAT GAC TGC AAG AAA GAA GGC GAA TGG AAG       156
Ile Lys Ala Thr Val Phe Asp Asp Cys Lys Lys Glu Gly Glu Trp Lys
     20                  25                  30

ATA ATG CTT TTA GAT GAA TTT ACC ACT AAG CTT TTG GCA TCG TGT TGC       204
Ile Met Leu Leu Asp Glu Phe Thr Thr Lys Leu Leu Ala Ser Cys Cys
 35                  40                  45

AAA ATG ACA GAT CTT CTA GAA GAA GGT ATT ACT GTT GTA GAG AAT ATT       252
Lys Met Thr Asp Leu Leu Glu Glu Gly Ile Thr Val Val Glu Asn Ile
 50                  55                  60                  65

TAT AAG AAC CGT GAA CCT GTC AGA CAA ATG AAA GCT CTT TAT TTC ATC       300
Tyr Lys Asn Arg Glu Pro Val Arg Gln Met Lys Ala Leu Tyr Phe Ile
             70                  75                  80

ACT CCG ACA TCA AAG TCT GTA GAT TGT TTC TTA CAT GAT TTT GCA AGT       348
Thr Pro Thr Ser Lys Ser Val Asp Cys Phe Leu His Asp Phe Ala Ser
         85                  90                  95

AAA TCG GAG AAC AAG TAT AAA GCA GCA TAT ATT TAC TTC ACT GAC TTT       396
Lys Ser Glu Asn Lys Tyr Lys Ala Ala Tyr Ile Tyr Phe Thr Asp Phe
        100                 105                 110

TGC CCT GAT AAT CTC TTT AAC AAA ATT AAG GCT TCT TGC TCC AAG TCA       444
Cys Pro Asp Asn Leu Phe Asn Lys Ile Lys Ala Ser Cys Ser Lys Ser
    115                 120                 125

ATA AGA AGA TGT AAA GAA ATA AAT ATT TCC TTC ATT CCA CAT GAA TCT       492
Ile Arg Arg Cys Lys Glu Ile Asn Ile Ser Phe Ile Pro His Glu Ser
130                 135                 140                 145

CAG GTG TAT ACT CTT GAT GTA CCA GAT GCA TTC TAT TAC TGT TAT AGT       540
Gln Val Tyr Thr Leu Asp Val Pro Asp Ala Phe Tyr Tyr Cys Tyr Ser
                150                 155                 160

CCA GAC CCT GGT AAT GCA AAG GGA AAA GAT GCC ATT ATG GAA ACA ATG       588
Pro Asp Pro Gly Asn Ala Lys Gly Lys Asp Ala Ile Met Glu Thr Met
            165                 170                 175

GCT GAC CAG ATA GTT ACA GTG TGT GCC ACC TTG GAT GAA AAT CCC GGA       636
Ala Asp Gln Ile Val Thr Val Cys Ala Thr Leu Asp Glu Asn Pro Gly
        180                 185                 190

GTA AGA TAT AAA AGT AAA CCT CTA GAT AAT GCC AGT AAG CTT GCA CAG       684
Val Arg Tyr Lys Ser Lys Pro Leu Asp Asn Ala Ser Lys Leu Ala Gln
    195                 200                 205
```

```
CTT GTT GAA AAA AAG CTT GAA GAC TAC TAC AAG ATT GAT GAA AAG AGC    732
Leu Val Glu Lys Lys Leu Glu Asp Tyr Tyr Lys Ile Asp Glu Lys Ser
210                 215                 220                 225

CTA ATA AAG GGT AAA ACT CAT TCA CAG CTC TTA ATA ATT GAT CGT GGC    780
Leu Ile Lys Gly Lys Thr His Ser Gln Leu Leu Ile Ile Asp Arg Gly
            230                 235                 240

TTT GAT CCT GTG TCC ACT GTC CTG CAT GAA CTG ACC TTT CAG GCA ATG    828
Phe Asp Pro Val Ser Thr Val Leu His Glu Leu Thr Phe Gln Ala Met
                245                 250                 255

GCA TAT GAT CTA CTA CCA ATT GAG AAT GAT ACA TAC AAA TAT AAA ACA    876
Ala Tyr Asp Leu Leu Pro Ile Glu Asn Asp Thr Tyr Lys Tyr Lys Thr
        260                 265                 270

GAT GGA AAA GAA AAG GAG GCC ATC CTT GAA GAA GAA GAT GAC CTC TGG    924
Asp Gly Lys Glu Lys Glu Ala Ile Leu Glu Glu Glu Asp Asp Leu Trp
275                 280                 285

GTT AGA ATT CGA CAT CGA CAT ATT GCG GTT GTG TTA GAG GAA ATT CCC    972
Val Arg Ile Arg His Arg His Ile Ala Val Val Leu Glu Glu Ile Pro
290                 295                 300                 305

AAG CTT ATG AAA GAA ATT TCA TCA ACA AAG AAA GCA ACA GAA GGA AAG   1020
Lys Leu Met Lys Glu Ile Ser Ser Thr Lys Lys Ala Thr Glu Gly Lys
            310                 315                 320

ACA TCA CTT AGT GCT CTT ACC CAG CTG ATG AAA AAG ATG CCC CAT TTC   1068
Thr Ser Leu Ser Ala Leu Thr Gln Leu Met Lys Lys Met Pro His Phe
                325                 330                 335

CGA AAA CAG ATT ACT AAG CAA GTT GTC CAT CTT AAC TTA GCA GAA GAT   1116
Arg Lys Gln Ile Thr Lys Gln Val Val His Leu Asn Leu Ala Glu Asp
        340                 345                 350

TGC ATG AAT AAG TTC AAG CTT AAT ATA GAA AAG CTC TGC AAA ACT GAA   1164
Cys Met Asn Lys Phe Lys Leu Asn Ile Glu Lys Leu Cys Lys Thr Glu
355                 360                 365

CAG GAC CTG GCA CTT GGA ACT GAT GCA GAA GGA CAG AAG GTG AAA GAT   1212
Gln Asp Leu Ala Leu Gly Thr Asp Ala Glu Gly Gln Lys Val Lys Asp
370                 375                 380                 385

TCC ATG CGA GTA CTC CTT CCA GTT CTA CTC AAC AAA AAT CAT GAT AAT   1260
Ser Met Arg Val Leu Leu Pro Val Leu Leu Asn Lys Asn His Asp Asn
            390                 395                 400

TGT GAT AAA ATA AGA GCA ATT CTA CTT TAT ATC TTC AGT ATT AAT GGA   1308
Cys Asp Lys Ile Arg Ala Ile Leu Leu Tyr Ile Phe Ser Ile Asn Gly
                405                 410                 415

ACT ACG GAA GAA AAT TTG GAC AGG TTG ATC CAG AAT GTA AAG ATA GAA   1356
Thr Thr Glu Glu Asn Leu Asp Arg Leu Ile Gln Asn Val Lys Ile Glu
        420                 425                 430

AAT GAG AGT GAC ATG ATT CGT AAC TGG AGT TAC CTT GGT GTT CCC ATT   1404
Asn Glu Ser Asp Met Ile Arg Asn Trp Ser Tyr Leu Gly Val Pro Ile
435                 440                 445

GTT CCC CAA TCT CAA CAA GGC AAA CCG TTA AGA AAG GAT CGG TCT GCA   1452
Val Pro Gln Ser Gln Gln Gly Lys Pro Leu Arg Lys Asp Arg Ser Ala
450                 455                 460                 465

GAA GAA ACT TTT CAG CTC TCT CGG TGG ACA CCT TTT ATC AAA GAT ATT   1500
Glu Glu Thr Phe Gln Leu Ser Arg Trp Thr Pro Phe Ile Lys Asp Ile
            470                 475                 480

ATG GAG GAT GCT ATT GAT AAT AGA TTA GAT TCA AAA GAA TGG CCA TAT   1548
Met Glu Asp Ala Ile Asp Asn Arg Leu Asp Ser Lys Glu Trp Pro Tyr
                485                 490                 495

TGT TCC CAG TGT CCA GCA GTA TGG AAT GGT TCA GGA GCT GTA AGT GCT   1596
Cys Ser Gln Cys Pro Ala Val Trp Asn Gly Ser Gly Ala Val Ser Ala
        500                 505                 510

CGC CAG AAA CCC AGA GCT AAT TAT TTA GAA GAC CGA AAA AAT GGG TCA   1644
Arg Gln Lys Pro Arg Ala Asn Tyr Leu Glu Asp Arg Lys Asn Gly Ser
515                 520                 525
```

-continued

```
AAG CTG ATT GTT TTT GTA ATT GGA GGG ATC ACA TAC TCT GAA GTG CGT         1692
Lys Leu Ile Val Phe Val Ile Gly Gly Ile Thr Tyr Ser Glu Val Arg
530                 535                 540                 545

TGT GCT TAT GAA GTT TCT CAG GCA CAT AAA TCC TGT GAA GTT ATT ATT         1740
Cys Ala Tyr Glu Val Ser Gln Ala His Lys Ser Cys Glu Val Ile Ile
                550                 555                 560

GGT TCT ACA CAT GTT TTA ACA CCC AAA AAG CTG TTG GAT GAT ATA AAG         1788
Gly Ser Thr His Val Leu Thr Pro Lys Lys Leu Leu Asp Asp Ile Lys
            565                 570                 575

ATG CTG AAT AAA CCC AAG GAT AAA GTC TCC TTA ATT AAA GAT GAATAGCA        1838
Met Leu Asn Lys Pro Lys Asp Lys Val Ser Leu Ile Lys Asp Glu
        580                 585                 590

TTTCTTTTTG GAGGGTTTAG AGATTCTTAC TAATATGTTG AACTAAAATAGAAAGAAAAT        1898

GTTGCTGTCA TGTAATTTAA ACAATGTAAA TATTTTATGG AATAATGGCTTTTCAAATAC        1958

ATTTCTTAAG GAACTGTTTA TGATTATTAC TGGATTTGTC ATTTTTGATAATTTAAATAT        2018

TGCTGCTGCT TTGTAGATGA TGAGAAGAAA TGTTAAAGTG CTTTCTAAAAGGAAATTTTT       2078

TCACCTTTGG AGGAGAATAT ATTAGAGTTG TGGGTAATTT TTCACAGCCACCTATGTACA        2138

TACTAATTAC CCATTGGATA CTTATATCTA AAAGTCTCAT GCTGAAGTATAGTTTTTGGG       2198

AAAGAATGAT TTTAAATAAA GAGATTGTAA AGTAAAAAA CTGTAAATGTATATGTATGA        2258

TAGAATTGTT TCCTCTAAGT GTAGTTTTTC TTTCAACTAA AATTCAGTTTATGTGTAAAA       2318

TAATTCAGTC ATTAATAGAA ATGGAGTGAT TCACAGTGT GTACTGTTTTGCCACATACT        2378

TCTAAAGAAC ACAATTTTAT ATAATTTTGA AATCATGTAT GTTTAAATTAGAAAACCAAA       2438

AATCATGAAC ATTCTAAGAG AAAATAAATA TAGAATTTAA AAAATTAAAAAAAAAAAAA        2498

AAAAAA                                                                  2504
```

(2) INFORMATION FOR SEQ ID NO:2:

(i) SEQUENCE CHARACTERISTICS:
        (A) LENGTH: 592 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO:2:

```
Met Ala Pro Pro Val Ala Glu Arg Gly Leu Lys Ser Val Val Trp Gln
1               5                   10                  15

Lys Ile Lys Ala Thr Val Phe Asp Asp Cys Lys Lys Glu Gly Glu Trp
            20                  25                  30

Lys Ile Met Leu Leu Asp Glu Phe Thr Thr Lys Leu Leu Ala Ser Cys
        35                  40                  45

Cys Lys Met Thr Asp Leu Leu Glu Glu Gly Ile Thr Val Val Glu Asn
    50                  55                  60

Ile Tyr Lys Asn Arg Glu Pro Val Arg Gln Met Lys Ala Leu Tyr Phe
65              70                  75                  80

Ile Thr Pro Thr Ser Lys Ser Val Asp Cys Phe Leu His Asp Phe Ala
            85                  90                  95

Ser Lys Ser Glu Asn Lys Tyr Lys Ala Ala Tyr Ile Tyr Phe Thr Asp
                100                 105                 110

Phe Cys Pro Asp Asn Leu Phe Asn Lys Ile Lys Ala Ser Cys Ser Lys
            115                 120                 125
```

-continued

Ser Ile Arg Arg Cys Lys Glu Ile Asn Ile Ser Phe Ile Pro His Glu
130                 135                 140

Ser Gln Val Tyr Thr Leu Asp Val Pro Asp Ala Phe Tyr Cys Tyr
145                 150                 155                 160

Ser Pro Asp Pro Gly Asn Ala Lys Gly Lys Asp Ala Ile Met Glu Thr
                165                 170                 175

Met Ala Asp Gln Ile Val Thr Val Cys Ala Thr Leu Asp Glu Asn Pro
            180                 185                 190

Gly Val Arg Tyr Lys Ser Lys Pro Leu Asp Asn Ala Ser Lys Leu Ala
        195                 200                 205

Gln Leu Val Glu Lys Lys Leu Glu Asp Tyr Tyr Lys Ile Asp Glu Lys
    210                 215                 220

Ser Leu Ile Lys Gly Lys Thr His Ser Gln Leu Leu Ile Ile Asp Arg
225                 230                 235                 240

Gly Phe Asp Pro Val Ser Thr Val Leu His Glu Leu Thr Phe Gln Ala
                245                 250                 255

Met Ala Tyr Asp Leu Leu Pro Ile Glu Asn Asp Thr Tyr Lys Tyr Lys
            260                 265                 270

Thr Asp Gly Lys Glu Lys Glu Ala Ile Leu Glu Glu Asp Asp Leu
        275                 280                 285

Trp Val Arg Ile Arg His Arg His Ile Ala Val Val Leu Glu Glu Ile
290                 295                 300

Pro Lys Leu Met Lys Glu Ile Ser Ser Thr Lys Lys Ala Thr Glu Gly
305                 310                 315                 320

Lys Thr Ser Leu Ser Ala Leu Thr Gln Leu Met Lys Lys Met Pro His
                325                 330                 335

Phe Arg Lys Gln Ile Thr Lys Gln Val Val His Leu Asn Leu Ala Glu
            340                 345                 350

Asp Cys Met Asn Lys Phe Lys Leu Asn Ile Glu Lys Leu Cys Lys Thr
        355                 360                 365

Glu Gln Asp Leu Ala Leu Gly Thr Asp Ala Glu Gly Gln Lys Val Lys
    370                 375                 380

Asp Ser Met Arg Val Leu Leu Pro Val Leu Leu Asn Lys Asn His Asp
385                 390                 395                 400

Asn Cys Asp Lys Ile Arg Ala Ile Leu Leu Tyr Ile Phe Ser Ile Asn
                405                 410                 415

Gly Thr Thr Glu Glu Asn Leu Asp Arg Leu Ile Gln Asn Val Lys Ile
            420                 425                 430

Glu Asn Glu Ser Asp Met Ile Arg Asn Trp Ser Tyr Leu Gly Val Pro
        435                 440                 445

Ile Val Pro Gln Ser Gln Gln Gly Lys Pro Leu Arg Lys Asp Arg Ser
450                 455                 460

Ala Glu Glu Thr Phe Gln Leu Ser Arg Trp Thr Pro Phe Ile Lys Asp
465                 470                 475                 480

Ile Met Glu Asp Ala Ile Asp Asn Arg Leu Asp Ser Lys Glu Trp Pro
                485                 490                 495

Tyr Cys Ser Gln Cys Pro Ala Val Trp Asn Gly Ser Gly Ala Val Ser
            500                 505                 510

Ala Arg Gln Lys Pro Arg Ala Asn Tyr Leu Glu Asp Arg Lys Asn Gly
        515                 520                 525

Ser Lys Leu Ile Val Phe Val Ile Gly Gly Ile Thr Tyr Ser Glu Val
530                 535                 540

Arg Cys Ala Tyr Glu Val Ser Gln Ala His Lys Ser Cys Glu Val Ile
545                 550                 555                 560

```
Ile Gly Ser Thr His Val Leu Thr Pro Lys Lys Leu Leu Asp Asp Ile
                565             570             575

Lys Met Leu Asn Lys Pro Lys Asp Lys Val Ser Leu Ile Lys Asp Glu
            580             585             590
```

What is claimed is:

1. An isolated DNA molecule comprising nucleotides 58–1833, inclusive, of SEQ ID NO:1, or a degenerate variant thereof.

2. The isolated DNA of claim 1, wherein the DNA encodes a protein whose amino acid sequence is SEQ ID NO:2.

3. An isolated DNA comprising SEQ ID NO:1 or a degenerate variant thereof.

4. A vector comprising the DNA of claim 1.

5. A vector comprising the DNA of claim 3.

6. The vector of claim 4, wherein said DNA is operably linked to an expression control sequence, said expression control sequence comprising a promoter.

7. The vector of claim 5, wherein said DNA is operably linked to an expression control sequence, said expression control sequence comprising a promoter.

8. A cell comprising the DNA of claim 1.

9. A cell comprising the DNA of claim 3.

10. A method of producing a platelet secretory transport protein, the method comprising the steps of:

(a) culturing a cell transformed with an isolated DNA comprising the coding sequence of SEQ ID NO:1, or a degenerate variant thereof; and (b) collecting the protein encoded by the coding sequence of SEQ ID NO: 1.

* * * * *